United States Patent [19]
Vignali et al.

[11] Patent Number: 5,652,364
[45] Date of Patent: Jul. 29, 1997

[54] PROCESS FOR THE PREPARATION OF 2,2,6,6-TETRAMETHYL-4-PIPERIDYLOXY-1,3,5-TRIAZINES WITH TWO OR MORE TRIAZINE RINGS

[75] Inventors: Graziano Vignali, Sasso Marconi; Fabrizio Guizzardi, Bologna; Graziano Zagnoni, Vergato; Roberto Scrima, Bologna, all of Italy

[73] Assignee: Ciba-Geigy Corporation, Tarrytown, N.Y.

[21] Appl. No.: 514,341

[22] Filed: Aug. 10, 1995

Related U.S. Application Data

[63] Continuation of Ser. No. 163,232, Dec. 6, 1993, abandoned.

[30] Foreign Application Priority Data

Dec. 10, 1992 [IT] Italy .................... MI92A2802

[51] Int. Cl.$^6$ ............... C07D 403/12; C07D 403/06; C07D 403/14
[52] U.S. Cl. .................. 544/209; 540/553; 544/212; 544/219
[58] Field of Search .............. 540/275; 544/209, 544/212, 219

[56] References Cited

U.S. PATENT DOCUMENTS

| | | | |
|---|---|---|---|
| 3,925,376 | 12/1975 | Chalmers et al. | 544/219 |
| 4,108,829 | 8/1978 | Cassandrini et al. | 544/209 |
| 4,412,020 | 10/1983 | Loffelman et al. | 429/100 |
| 4,769,443 | 9/1988 | Cantatore | 528/423 |

FOREIGN PATENT DOCUMENTS

| | | |
|---|---|---|
| 0112690 | 7/1984 | European Pat. Off. . |
| 0117229 | 8/1984 | European Pat. Off. . |
| 0389431 | 9/1990 | European Pat. Off. . |
| 03995584 | 10/1990 | European Pat. Off. . |

OTHER PUBLICATIONS

J. Am. Chem. Soc. 73, 2999, 1951.
English Translation of EP 0117229, 1984.

*Primary Examiner*—Yogendra N. Gupta
*Attorney, Agent, or Firm*—Luther A.R. Hall; Michele Kovaleski

[57] ABSTRACT

Novel process for the preparation of 2,2,6,6-tetramethyl-4-piperidyloxy-1,3,5-triazines, based on the reaction of cyanuric chloride with $C_1$–$C_4$ alkanols or with sodium or potassium $C_1$–$C_4$ alkoxides and subsequent reaction with 2,2,6,6-tetramethyl-4-piperidinols in the presence of a transesterification catalyst.

The various reactions can be carried out in the same reactor, without isolation of the intermediates.

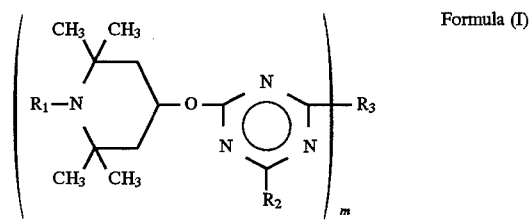

Formula (I)

15 Claims, No Drawings

PROCESS FOR THE PREPARATION OF 2,2,6,6-TETRAMETHYL-4-PIPERIDYLOXY-1,3,5-TRIAZINES WITH TWO OR MORE TRIAZINE RINGS

This application is a continuation of application Ser. No. 08/163,232 filed Dec. 6, 1993, now abandoned.

The present invention relates to a novel process for the preparation of 2,2,6,6-tetramethyl-4-piperidyloxy-1,3,5-triazines with two or more triazine rings, useful as stabilisers for organic materials, and the present invention also relates to various novel derivatives of 2,2,6,6-tetramethyl-4-piperidyloxy-1,3,5-triazine.

The preparation of these compounds has been described in EP Patent 395 584 and comprises the reaction, in any order and in an inert organic solvent, of cyanuric chloride with 2,2,6,6-tetramethyl-4-piperidinols and various polyamines in the presence of an inorganic base such as sodium hydroxide, or the reaction of 2,2,6,6-tetramethyl-4-piperidinols in the form of sodium alcoholates with cyanuric chloride and various polyamines.

U.S. Pat. No. 3,925,376 and EP 389,431 report analogous processes for the preparation of 2,2,6,6-tetramethyl-4-piperidyloxy-1,3,5-triazines with a single triazine ring.

The use of the sodium alcoholate of the 2,2,6,6-tetramethyl-4-piperidinols makes it possible to obtain satisfactory yields in some cases, but such a process, when carried out on a large scale, implies the use of large quantities of metallic sodium or sodium hydride, which require substantial precautions in order to avoid the risk of fires or explosions.

The use of 2,2,6,6-tetramethyl-4-piperidinols and sodium hydroxide eliminates the above risks but gives, on the other hand, very low yields.

These difficulties have hindered the production and use on an industrial scale of 2,2,6,6-tetramethyl-4-piperidyloxy-1,3,5-triazines as stabilisers for organic materials.

It was consequently desirable to have available a process for the preparation of 2,2,6,6-tetramethyl-4-piperidyloxy-1,3,5-triazines in higher yields and without the dangers due to the use of alkali metals or hydrides thereof.

It has now been found, surprisingly, that the 2,2,6,6-tetramethyl-4-piperidyloxy-1,3,5-triazines can be obtained constantly in higher yields as compared with the state of the art, without the use of alkali metals or hydrides thereof, by means of a novel process based on the reaction of cyanuric chloride with $C_1$–$C_4$alkanols or with sodium or potassium $C_1$–$C_4$alkoxides and polyamines to form $C_1$–$C_4$alkoxytriazine derivatives which, by reaction with 2,2,6,6-tetramethyl-4-piperidinols in the presence of a transesterification catalyst, easily give the corresponding 2,2,6,6-tetramethyl-4-piperidyloxy-1,3,5-triazines, it being possible to carry out the various reactions in the same reactor without isolation of the intermediates.

The constantly high yields of 2,2,6,6-tetramethyl-4-piperidyloxy-1,3,5-triazines thus obtained and the possibility of carrying out the reaction in a single reactor make the process of the present invention highly advantageous and therefore suitable for use on an industrial scale.

In particular, the present invention relates to a novel process for the preparation of compounds of the formula (I)

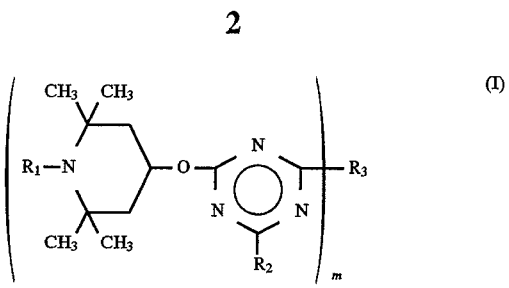

in which $R_1$ is hydrogen, $C_1$–$C_8$alkyl, $C_1$–$C_{18}$alkoxy, $C_5$–$C_{12}$cycloalkoxy, $C_3$–$C_6$alkenyl or $C_7$–$C_9$phenylalkyl which is unsubstituted or mono-, di- or tri-substituted on the phenyl by $C_1$–$C_4$alkyl; $R_2$ is a group of the formula (II)

or a group

where $R_4$ and $R_5$ which can be identical or different are hydrogen, $C_1$–$C_{18}$alkyl, $C_5$–$C_{12}$cycloalkyl which is unsubstituted or mono-, di- or tri-substituted by $C_1$–$C_4$alkyl; $C_7$–$C_9$phenylalkyl which is unsubstituted or mono-, di- or tri-substituted on the phenyl by $C_1$–$C_4$alkyl; tetrahydrofurfuryl, $C_2$–$C_4$alkyl substituted in the 2-, 3- or 4-position by $C_1$–$C_8$alkoxy or by di($C_1$–$C_4$alkyl)amino; or a group of the formula (III)

where $R_6$ is as defined for $R_1$, or

is a 5- to 7-membered heterocyclic group, m is an integer from 2 to 6 and, if m is 2, $R_3$ is one of the groups of the formulae (IVa)–(IVc)

in which $R_7$, $R_9$, $R_{11}$ and $R_{12}$ which can be identical or different are hydrogen, $C_1$–$C_{18}$alkyl, $C_5$–$C_{12}$cycloalkyl which is unsubstituted or mono-, di- or tri-substituted by $C_1$–$C_4$alkyl; $C_7$–$C_9$phenylalkyl which is unsubstituted or mono-, di- or tri-substituted on the phenyl by $C_1$–$C_4$alkyl; or a group of the formula (III), $R_8$ is $C_2$–$C_{12}$alkylene, $C_4$–$C_{12}$alkylene interrupted by 1, 2 or 3 oxygen atoms; $C_5$–$C_7$cycloalkylene, $C_1$–$C_7$cycloalkylenedi($C_1$–$C_4$alkylene), $C_5$–$C_4$alkylenedi($C_5$–$C_7$cycloalkylene), phenylene or xylylene, $R_{10}$ is hydrogen or methyl, n is zero or 1, p and q which can be identical or different are integers from 2 to 6 and r is zero or 1, and, if m is 3, 4, 5 or 6, $R_3$ is a group of the formula (V)

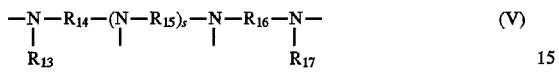
(V)

in which $R_{13}$ and $R_{17}$ which can be identical or different are as defined above for $R_7$, $R_9$, $R_{11}$ and $R_{12}$; $R_{14}$, $R_{15}$ and $R_{16}$ which can be identical or different are $C_2$–$C_6$alkylene and s is zero, 1, 2 or 3, and, if m is 3, $R_3$ can also be a group of the formula (VIa) or (VIb)

(VIa)

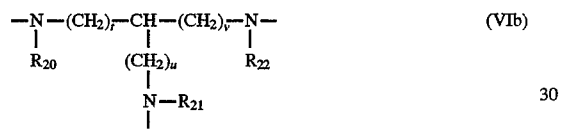
(VIb)

in which $R_{18}$ is $C_2$–$C_6$alkylene, $R_{19}$, $R_{20}$, $R_{21}$ and $R_{22}$ which can be identical or different are as defined above for $R_7$, $R_9$, $R_{11}$ and $R_{12}$, t and v which can be identical or different are integers from 2 to 6 and u is zero or 1, this process comprising:

I-a) the reaction of cyanuric chloride with a $C_1$–$C_4$alkanol and, if $R_2$ is a group

also a compound of the formula (VII)

(VII)

in which $R_4$ and $R_5$ are as defined above, in the presence of a compound of the formula (VIII) as HCl interceptor

(VIII)

in which $R_1$ is as defined above, to give an intermediate of the formula (IX)

(IX)

in which A is $C_1$–$C_4$alkoxy and $R_2'$ is $C_1$–$C_4$alkoxy or, if $R_2$ is a group

$R_2'$ is

I-b) the reaction of the intermediate of the formula (IX) with a compound of the formula (X)

$R_3$—(H)$_m$  (X)

in which $R_3$ and m are as defined above, to give—after neutralisation of the reaction mixture with sodium hydroxide, potassium hydroxide, sodium $C_1$–$C_4$alkoxide or potassium $C_1$–$C_4$alkoxide—an intermediate of the formula (XI)

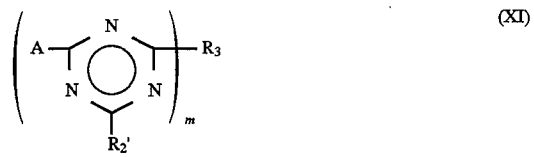
(XI)

together with a compound of the formula (VIII) as the free base; and

I-c) the reaction of the intermediate of the formula (XI) with a compound of the formula (VIII) in the presence of a transesterification catalyst;

or comprising

II-a) the reaction of cyanuric chloride with a compound of the formula (X) and, if $R_2$ is a group

also with a compound of the formula (VII), in the presence of a compound of the formula (VIII) as HCl interceptor to give an intermediate of the formula (XII)

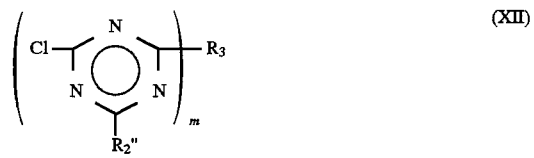
(XII)

in which $R_2''$ is Cl or, if $R_2$ is a group

$R_2''$ is

and m and $R_3$ are as defined above;

II-b) the reaction of the intermediate of the formula (XII) with sodium $C_1$–$C_4$alkoxide or potassium $C_1$–$C_4$alkoxide to give an intermediate of the formula (XI) together with a compound of the formula (VIII) as the free base; and II-c) the reaction of the intermediate of the formula (XI) with a compound of the formula (VIII) in the presence of a transesterification catalyst;

the reactions from I-a) to I-c) or from II-a) to II-c) being carried out at a temperature of between −20° C. and 180° C. in an inert organic solvent or, in the case of the reaction I-c) or II-c) also without solvent.

Examples of alkyl having not more than 18 carbon atoms are methyl, ethyl, propyl, isopropyl, butyl, 2-butyl, isobutyl, t-butyl, pentyl, 2-pentyl, hexyl, heptyl, octyl, 2-ethylhexyl, nonyl, decyl, undecyl, dodecyl, tridecyl, tetradecyl, hexadecyl and octadecyl.

$C_1$–$C_8$alkyl is preferred.

Examples of $C_2$–$C_4$alkyl substituted by $C_1$–$C_8$alkoxy are 2-methoxyethyl, 2-ethoxyethyl, 3-methoxypropyl, 3-ethoxypropyl, 3-butoxypropyl, 3-octoxypropyl and 4-methoxybutyl; 3-methoxypropyl and 3-ethoxypropyl are preferred.

Examples of $C_2$–$C_4$alkyl substituted by di($C_1$–$C_4$alkyl) amino, preferably dimethylamino or diethylamino, are 2-dimethylaminoethyl, 2-diethylaminoethyl, 3-dimethylaminopropyl, 3-diethylaminopropyl, 3-dibutylaminopropyl and 4-diethylaminobutyl.

Preferred examples of $C_1$–$C_4$alkoxy A and $R_2'$ are methoxy, ethoxy, propoxy, isoproxy, butoxy and isobutoxy; methoxy and ethoxy are particularly preferred.

Representative examples of $C_1$–$C_{18}$alkoxy $R_1$ and $R_6$ are methoxy, ethoxy, propoxy, isopropoxy, butoxy, isobutoxy, pentoxy, isopentoxy, hexoxy, heptoxy, octoxy, decyloxy, dodecyloxy, tetradecyloxy, hexadecyloxy and octadecyloxy.

$C_6$–$C_{12}$alkoxy, in particular heptoxy and octoxy, are preferred.

Representative examples of $C_5$–$C_{12}$cycloalkoxy $R_1$ and $R_6$ are cyclopentoxy, cyclohexoxy, cycloheptoxy, cyclooctoxy, cyclodecyloxy and cyclododecyloxy. Cyclopentoxy and cyclohexoxy are preferred.

Examples of substituted or unsubstituted $C_5$–$C_{12}$cycloalkyl are cyclopentyl, methylcyclopentyl, dimethylcyclopentyl, cyclohexyl, methylcyclohexyl, dimethylcyclohexyl, trimethylcyclohexyl, t-butylcyclohexyl, cyclooctyl, cyclodecyl and cyclododecyl. Cyclohexyl is preferred.

Examples of $C_3$–$C_6$alkenyl are allyl, 2-methylallyl, butenyl, pentenyl and hexenyl. Allyl is preferred.

Examples of $C_7$–$C_9$phenylalkyl, unsubstituted or substituted on the phenyl, are benzyl, methylbenzyl, dimethylbenzyl, t-butylbenzyl and 2-phenylethyl. Benzyl is preferred.

Representative examples of a 5-membered to 7-membered heterocyclic group

are 1-pyrrolidyl, 1-piperidyl, 4-morpholinyl, 4-methyl-1-piperazinyl and 1-hexahydroazepinyl. 4-Morpholinyl is preferred.

Examples of alkylene having not more than 12 carbon atoms are ethylene, propylene, trimethylene, tetramethylene, pentamethylene, 2,2-dimethyltrimethylene, hexamethylene, trimethylhexamethylene, decamethylene and dodecamethylene.

Representative examples of $C_4$–$C_{12}$alkylene interrupted by 1,2 or 3 oxygen atoms are 3-oxapentane-1,5-diyl, 4-oxaheptane-1,7-diyl, 4,7-dioxadecane-1,10-diyl, 4,9-dioxadodecane-1,12-diyl and 4,7,10-trioxatridecane-1,13-diyl.

Representative examples of groups containing 1 or 2 $C_5$–$C_7$cycloalkylene groups are cyclohexylene, methylcyclohexylene, cyclohexylenedimethylene and methylenedicyclohexylene.

Examples of $C_1$–$C_4$alkanols are methanol, ethanol, propanol, n-butanol or isobutanol, preferably methanol, ethanol or n-butanol.

Examples of sodium $C_1$–$C_4$alkoxide or potassium $C_1$–$C_4$alkoxide are sodium methoxide, sodium ethoxide, potassium methoxide and potassium ethoxide.

Sodium methoxide and sodium ethoxide are preferred.

The process of the present invention comprises a reaction in three stages, each of which requires a different temperature.

The first stage—reactions I-a), II-a)—is carried out, for example, at a temperature of between −20° C. and 40° C., preferably between −10° C. and 30° C.; the second stage—reactions I-b), II-b)—is carried out, for example, at a temperature of between 20° C. and 120° C., preferably between 20° C. and 100° C.; the third stage—reactions I-c), II-c)—is carried out, for example, at a temperature of between 120° C. and 180° C., preferably between 130° C. and 160° C.

In the reactions I-a) to I-c) or II-a) to II-c), the reagents are conveniently present in nearly stoichiometric quantities, but the monofunctional reagents can also be used in an excess of up to 50% of theory. If the reagent is $C_1$–$C_4$alkanol, this reagent can be used in quantities of up to 200% of theory.

In the definitions which follow, the variable m is always as defined in formula (I), and the ratios are molar ratios.

If $R_2$ is other than

the cyanuric chloride: $C_1$–$C_4$alkanol ratio in reaction I-a) goes, for example, from 1:2 to 1:6, preferably from 1:2 to 1:4; in reaction I-b), the intermediate (IX): compound (X) ratio goes, for example, from m:1 to [m(1+0.1)]:1, preferably from m:1 to [m(1+0.03)]:1 and, in reaction I-c), the intermediate (XI): compound (VIII) ratio goes, for example, from 1:2 m to 1:[2 m(1+0.6)], preferably from 1:2 m to 1:[2 m(1+0.2)].

If $R_2$ is a group

the cyanuric chloride: $C_1$–$C_4$alkanol: compound (VII) ratio in reaction I-a) goes, for example, from 1:1:1 to 1:3:1.1, preferably from 1:1:1 to 1:2:1.03; in reaction I-b), the intermediate (IX): compound (X) ratio goes, for example, from m:1 to [m(1+0.1)]:1, preferably from m:1 to [m(1+0.03)]:1; and in reaction I-c), the intermediate (XI): compound (VIII) ratio goes, for example, from 1:m to 1:[m(1+0.5)], preferably from 1:m to 1:[m(1+0.2)].

The cyanuric chloride: liberated hydrochloric acid interceptor (VIII) ratio in reaction I-a) goes, for example, from 1:1 to 1:3, preferably from 1:1 to 1:2.4.

If $R_2$ is other than

the cyanuric chloride: compound (X) ratio in reaction II-a) goes, for example, from m:1 to [m(1+0.1)]:1, preferably from m:1 to [m(1+0.03)]:1; in reaction II-b), the intermediate (XII): $C_1$–$C_4$alkoxide ratio goes, for example, from 1:2 m to 1:[2 m(1+2)], preferably from 1:2 m to 1:[2 m(1+1)] and, in reaction II-c), the intermediate (XI): compound (VIII) ratio goes, for example, from 1:2 m to 1:[2 m(1+0.5)], preferably from 1:2 m to 1:[2 m(1+0.2)].

If $R_2$ is a group

the cyanuric chloride: compound (X): compound (VII) ratio in the reaction II-a) goes, for example, from m:1:m to [m(1+0.1)]:1:[m(1+0.1)], preferably from m:1:m to [m(1+0.03)]:1:[m(1+0.03)]; in reaction II-b), the intermediate (XII): $C_1$–$C_4$alkoxide ratio goes, for example, from 1:m to 1:[m(1+2)], preferably from 1:m to 1:[m(1+1)]; and in reaction II-c), the intermediate (XI): compound (VII) ratio goes, for example, from 1:m to 1:[m(1+0.5)], preferably from 1:m to 1:[m(1+0.2)].

The cyanuric chloride:liberated hydrochloric acid interceptor (VIII) ratio in reaction II-a) goes, for example, from 1:1 to 1:3, preferably from 1:1 to 1:2.4

In particular, the compounds of the formula (VIII) are preferably used in an excess of from 10 to 50% over theory, in order to accelerate the transesterification rate—reactions I-c) and II-c)—the excess being easily recoverable from the reaction mixture by distillation under reduced pressure or by extraction with water.

The compound of the formula (VIII) can be introduced entirely at the start of the reaction or can be added during the diverse stages, if required. The total duration of the process depends therefore, apart from the temperature of the diverse reactions and the nature of the reagents employed, also on the excess of piperidinol of the formula (VIII) employed. The progress of the reaction can be followed by HPLC (high-performance liquid chromatography).

When the reaction is complete, the resulting mixture is washed with water in order to remove the sodium or potassium chloride and a part of the unreacted piperidinols of the formula (VIII).

The solvent and the remaining excess piperidinol are then removed by distillation at reduced pressure, and the residue is purified by conventional methods, for example by crystallisation from suitable solvents.

In some cases, the compounds of the formula (I) are obtained directly at a high degree of purity, so that they do not require any purification.

The transesterification catalysts which can be used according to the present invention are, for example, an alkali metal or a $C_1$–$C_4$alkoxide, hydride or amide of an alkali metal.

The preferred catalysts are sodium methoxide, sodium hydride and lithium amide.

Examples of inert organic solvents which can be used according to the present invention are benzene, toluene, xylene, trimethylbenzene, tetrahydrofuran, dioxane, dibutyl ether, 1,2-dimethoxyethane, 1,2-diethoxyethane, bis(2-methoxyethyl) ether, bis(2-ethoxyethyl) ether or mixtures in any ratio, preferably from 3:1 to 1:3 by volume, of the aromatic hydrocarbons cited above with tertiary alcohols such as t-butyl alcohol and t-amyl alcohol.

The preferred solvents are toluene, xylene and 3:1 to 1:3 mixtures by volume of toluene or xylene with t-amyl alcohol.

The reactions from I-a) to I-c) or from II-a) to II-c) can be carried out in the same solvents or in different solvents, and with or without isolation of the intermediates (IX), (XI) or (XII) at the end of each reaction.

The compounds used for the preparation of the compounds of the formula (I) are commercially available or can easily be prepared by known processes.

The process of the present invention is distinguished from the processes of the state of the art by the use of the piperidinols of the formula (VIII), in the first stages of the reaction, as temporary acceptors of the liberated hydrochloric acid, the hydrochlorides formed being subsequently neutralised by sodium or potassium hydroxide or $C_1$–$C_4$alkoxide to re-form the free bases which thereby become available again for the transesterification reaction with the alkoxytriazine compound.

The use of the piperidinols of the formula (VIII) as temporary bases makes it possible to avoid the hydrolytic reactions of the chlorotriazines, which normally occur with the direct use of bases such as sodium or potassium carbonate, and thus makes it possible to obtain the compounds of the formula (I) in very high yields.

A further point distinguishing the present invention from the state of the art is the transesterification reaction of the alkoxy derivatives of the 1,3,5-triazine with the piperidinols of the formula (VIII).

The transesterification reaction of the alkoxy derivatives of the 1,3,5-triazine with alcohols and glycols in the presence of a transesterification catalyst is known (J.A.C.S. 73, 2999 (1951), U.S. Pat No. 4,412,020 and U.S. Pat. No. 4,769,443), but has never been used for the preparation of the compounds of the formula (I).

$R_1$ and $R_6$ are preferably hydrogen, $C_1$–$C_4$alkyl, $C_6$–$C_{12}$alkoxy, $C_5$–$C_8$cycloalkoxy, allyl or benzyl, in particular hydrogen or methyl.

Those compounds of the formula (I) are preferred in which $R_2$ is a group of the formula (II) or a group

where $R_4$ and $R_5$ which can be identical or different are hydrogen, $C_1$–$C_{12}$alkyl, $C_5$–$C_8$cycloalkyl which is unsubstituted or mono-, di- or trisubstituted by $C_1$–$C_4$alkyl; benzyl, tetrahydrofurfuryl, $C_2$–$C_3$alkyl substituted in the 2- or 3-position by $C_1$–$C_4$alkoxy or by di($C_1$–$C_4$alkyl)amino or a group of the formula (III) or

is 1-pyrrolidyl, 1-piperidyl, 4-morpholinyl, 4-methyl-1-piperazinyl or 1-hexahydroazepinyl, m is an integer from 2 to 6 and, if m is 2, $R_3$ is one of the groups of the formula (IVa)–(IVc) in which $R_7$, $R_9$, $R_{11}$ and $R_{12}$ which can be identical or different are hydrogen, $C_1$–$C_{12}$alkyl, $C_5$–$C_8$cycloalkyl which is unsubstituted or mono-, di- or tri-substituted by $C_1$–$C_4$alkyl; benzyl or a group of the formula (III), $R_8$ is $C_2$–$C_{10}$alkylene, $C_4$–$C_{10}$alkylene interrupted by 1, 2 or 3 oxygen atoms; cyclohexylene, cyclohexylenedimethylene, methylenedicyclohexylene or xylylene, $R_{10}$ is hydrogen or methyl, n is zero or 1, p and q which can be identical or different are an integer from 2 to 6 and R is zero or 1, and, if m is 3, 4, 5 or 6, $R_3$ is a group of the formula (V) in which $R_{13}$ and $R_{17}$ which can be identical or different are as defined above for $R_7$, $R_9$, $R_{11}$ and $R_{12}$; $R_{14}$, $R_{15}$ and $R_{16}$ which can be identical or different are $C_2$–$C_6$alkylene and s is zero or 1, 2 or 3, and, if m is 3, $R_3$ can also be a group of the formula (VIa) or (VIb) in which $R_{18}$ is $C_2$–$C_6$alkylene, $R_{19}$, $R_{20}$, $R_{21}$, $R_{22}$ which can be identical or different are as defined above for $R_7$, $R_9$, $R_{11}$ and $R_{12}$, t and v which can be identical or different are integers from 2 to 6 and u is zero or 1.

Those compounds of the formula (I) are particularly preferred in which $R_2$ is a group of the formula (II) or a group

where $R_4$ and $R_5$ which can be identical or different are hydrogen, $C_1$–$C_{10}$alkyl, cyclohexyl which is unsubstituted or mono-, di- or tri-substituted by $C_1$–$C_4$alkyl; benzyl, tetrahydrofurfuryl, $C_2$–$C_3$alkyl substituted in the 2- or 3-position by methoxy, by ethoxy, by dimethylamino or by diethylamino; or a group of the formula (III), or

is 4-morpholinyl, m is an integer from 2 to 6 and, if m is 2, $R_3$ is one or the groups of the formulae (IVa)–(IVc) in which $R_7$, $R_9$, $R_{11}$ and $R_{12}$ which can be identical or different are hydrogen, $C_1$–$C_{10}$alkyl, cyclohexyl which is unsubstituted or mono-, di- or tri-substituted by $C_1$–$C_4$alkyl; benzyl or a group of the formula (III), $R_8$ is $C_2$–$C_8$alkylene, $C_4$–$C_{10}$alkylene interrupted by 1, 2 or 3 oxygen atoms; cyclohexylenedimethylene, methylenedicyclohexylene or xylylene, $R_{10}$ is hydrogen or methyl, n is zero or 1, p and q which can be identical or different are 2 or 3 and r is zero or 1 and, if m is 3, 4, 5 or 6, $R_3$ is a group of the formula (V) in which $R_{13}$ and $R_{17}$ which can be identical or different are as defined above for $R_7$, $R_9$, $R_{11}$ and $R_{12}$; $R_{14}$, $R_{15}$ and $R_{16}$ which can be identical or different are $C_2$–$C_6$alkylene and s is zero, 1, 2 or 3, and, if m is 3, $R_3$ can also be a group of the formula (VIa) or (VIb) in which $R_{18}$ is $C_2$–$C_3$alkylene, $R_{19}$, $R_{20}$, $R_{21}$ and $R_{22}$ which can be identical or different are as defined above for $R_7$, $R_9$, $R_{11}$ and $R_{12}$, t and v which can be identical or different are integers from 3 to 5 and u is zero or 1.

Those compounds of the formula (I) are of special interest in which $R_2$ is a group of the formula (II) or a group

where $R_4$ and $R_5$ which can be identical or different are $C_1$–$C_8$alkyl, cyclohexyl, benzyl, tetrahydrofurfuryl, $C_2$–$C_3$alkyl substituted in the 2- or 3-position by methoxy, by ethoxy, by dimethylamino or by diethylamino; or a group of the formula (III), or $R_5$ can also be hydrogen, or

is 4-morpholinyl, m is 2, 3 or 4 and, if m is 2, $R_3$ is one of the groups of the formulae (IVa)–(IVc) in which $R_7$, $R_9$, $R_{11}$ and $R_{12}$ which can be identical or different are $C_1$–$C_4$alkyl, cyclohexyl or a group of the formula (III), $R_8$ is $C_2$–$C_6$alkylene, $C_6$–$C_{10}$alkylene interrupted by 2 or 3 oxygen atoms; cyclohexylenedimethylene, methylenedicyclohexylene or xylylene, $R_{10}$ is hydrogen, n is zero, p and q which can be identical or different are 2 or 3 and r is zero or 1, and, if m is 3 or 4, $R_3$ is a group of the formula (V) in which $R_{13}$ and $R_{17}$ which can be identical or different are as defined above for $R_7$, $R_9$, $R_{11}$ and $R_{12}$, $R_{14}$, $R_{15}$ and $R_{16}$ which can be identical or different are $C_2$–$C_6$alkylene and s is zero or 1.

Those compounds of the formula (I) are of particular interest in which $R_1$ is hydrogen or methyl, $R_2$ is 2,2,6,6-tetramethyl-4-piperidyloxy or 1,2,2,6,6-pentamethyl-4-piperidyloxy, m is 2, 3 or 4 and, if m is 2, $R_3$ is a group of the formula (IVa) in which $R_7$ and $R_9$ which can be identical or different are cyclohexyl, 2,2,6,6-tetramethyl-4-piperidyl or 1,2,2,6,6-pentamethyl-4-piperidyl and $R_8$ is $C_2$–$C_6$alkylene, and, if m is 3 or 4, $R_3$ is a group of the formula (V) in which $R_{13}$ and $R_{17}$ which can be identical or different are as defined above for $R_7$ and $R_9$, $R_{14}$, $R_{15}$ and $R_{16}$ which can be identical or different are —$(CH_2)_{2-6}$ and s is zero or 1.

A further subject of the present invention is the following novel compounds:

1,5,8,12-tetrakis[2,4-bis(2,2,6,6-tetramethyl-4-piperidyloxy)triazin-6-yl]-1,12-bis(2,2,6,6-tetramethyl-4-piperidyl)-1,5,8,12-tetraazadodecane, 1,5,8,12-tetrakis[2,4-bis(1,2,2,6,6-pentamethyl-4-piperidyloxy)triazin-6-yl]-1,12-bis(2,2,6,6-tetramethyl-4-piperidyl)-1,5,8,12-tetraazadodecane, 1,5,8,12-tetrakis[2,4-bis(1,2,2,6,6-pentamethyl-4-piperidyloxy)triazin-6-yl]-1,12-bis(1,2,2,6,6-pentamethyl-4-piperidyl)-1,5,8,12-tetraazadodecane, 1,5,8,12-tetrakis[2,4-bis(1,2,2,6,6-pentamethyl-4-piperidyloxy)triazin-6-yl]-1,5,8,12-tetraazadodecane, 1,4,7,10-tetrakis[2,4-bis(2,2,6,6-tetramethyl-4-piperidyloxy)triazin-6-yl]-1,10-bis(2,2,6,6-tetramethyl-4-piperidyl)-1,4,7,10-tetraazadecane, 1,4,7,10-tetrakis[2,4-bis(1,2,2,6,6-pentamethyl-4-piperidyloxy)triazin-6-yl]-1,10-bis(2,2,6,6-tetramethyl-4-piperidyl)-1,4,7,10-tetraazadecane, 1,4,7,10-tetrakis[2,4-bis(1,2,2,6,6-pentamethyl-4-piperidyloxy)triazin-6-yl]-1,10-bis(1,2,2,6,6-pentamethyl-4-piperidyl)-1,4,7,10-tetraazadecane;

1,4,7,10-tetrakis[2,4-bis(2,2,6,6-tetramethyl-4-piperidyloxy)triazin-6-yl]-1,4,7,10-tetraazadecane, 1,4,7,10-tetrakis[2,4-bis(1,2,2,6,6-pentamethyl-4-piperidyloxy)triazin-6-yl]-1,4,7,10-tetraazadecane, 1,5,8,10-tetrakis[2-(2,2,6,6-tetramethyl-4-piperidyloxy)-4-[N-2,2,6,6-tetramethyl-4-piperidyl)-2,2,6,6-tetramethyl-4-piperidylamino)-triazin-6-yl]-1,12-bis(2,2,6,6-tetramethyl-4-piperidyl)-1,5,8,12-tetraazadodecane, 1,5,8,12-tetrakis[2-(2,2,6,6-tetramethyl-4-piperidyloxy)-4-[N-2,2,6,6-tetramethyl-4-piperidyl)-2,2,6,6-tetramethyl-4-piperidylamino)-triazin-6-yl]-1,5,8,12-tetraazadodecane, 1,5,8,12-tetrakis[2-(1,2,2,6,6-pentamethyl-4-piperidyloxy)-4-[N-1,2,2,6,6-pentamethyl-4-piperidyl)-1,2,2,6,6- pentamethyl-4-piperidylamino)-triazin-6-yl]-1,12-bis(2,2,6,6-tetramethyl-4-piperidyl)-1,5,8,12-tetraazadodecane, 1,5,8,12-tetrakis[2-(1,2,2,6,6-pentamethyl-4-piperidyloxy)-4-[N-(1,2,2,6,6-pentamethyl-4-piperidyl)-1,2,2,6,6-pentamethyl-4-piperidylamino]-triazin-6-yl]-1,12-bis(1,2,2,6,6-pentamethyl-4-piperidyl)-1,5,8,12-tetraazadodecane, 1,5,8,12-tetrakis[2-(1,2,2,6,6-pentamethyl-4-piperidyloxy)-4-[N-(1,2,2,6,6-pentamethyl-4-piperidyl)-1,2,2,6,6-pentamethyl-4-piperidylamino]-triazin-6-yl]-1,5,8,12-tetraazadodecane, 1,5,8,12-tetrakis[2-(1,2,2,6,6-pentamethyl-4-piperidyloxy)-4-[N-(2,2,6,6-tetramethyl-4-piperidyl)-2,2,6,6-tetramethyl-4-piperidylamino]-triazin-6-yl]-1,5,8,12-tetraazadodecane, 1,5,8,12-tetrakis[2-(1,2,2,6,6-pentamethyl-4-piperidyloxy)-4-[N-(2,2,6,6-tetramethyl-4-piperidyl)-2,2,6,6-tetramethyl-4-piperidylamino]-triazin-6-yl]-1,12-bis(2,2,6,6-tetramethyl-4-piperidyl)-1,5,8,12-tetraazadodecane, 1,5,8,12-tetrakis[2-(2,2,6,6-tetramethyl-4-piperidyloxy)-4-[N-(2,2,6,6-tetramethyl-4-piperidyl)-butylamino]-triazin-6-yl]-1,12-bis(2,2,6,6-tetramethyl-4-piperidyl)-1,5,8,12-tetraazadodecane, 1,5,8,12-tetrakis[2-(1,2,2,6,6-pentamethyl-4-piperidyloxy)-4-[N-(1,2,2,6,6-pentamethyl-4-piperidyl)-butylamino]-triazin-6-yl]-1,12-bis(1,2,2,6,6-pentamethyl-4-piperidyl)-1,5,8,12-tetraazadodecane, 1,5,8,12-tetrakis[2-(1,2,2,6,6-pentamethyl-4-piperidyloxy)-4-[N-(2,2,6,6-tetramethyl-4-piperidyl)-butylamino]-triazin-6-yl]-1,12-bis(2,2,6,6-tetramethyl-4-piperidyl)-1,5,8,12-tetraazadodecane, 1,5,8,12-tetrakis[2-(1,2,2,6,6-pentamethyl-4-piperidyloxy)-4-[N-(1,2,2,6,6-pentamethyl-4-piperidyl)-butylamino]-triazin-6-yl]-1,12-bis(2,2,6,6-tetramethyl-4-piperidyl)-1,5,8,12-tetraazadodecane, 1,5,8,12-tetrakis[2-(2,2,6,6-tetramethyl-4-piperidyloxy)-4-[N-(2,2,6,6-tetramethyl-4-piperidyl)-butylamino]-triazin-6-yl]-1,5,8,12-tetraazadodecane, 1,5,8,12-tetrakis[2-(1,2,2,6,6-pentamethyl-4-piperidyloxy)-4-[N-(1,2,2,6,6-pentamethyl-4-piperidyl)-butylamino]-triazin-6-yl]-1,5,8,12-tetraazadodecane, 1,4,7,10-tetrakis[2-(2,2,6,6-tetramethyl-4-piperidyloxy)-4-[N-(2,2,6,6-tetramethyl-4-piperidyl)-2,2,6,6-tetramethyl-4-piperidylamino]-triazin-6-yl]-1,10-bis(2,2,6,6-tetramethyl-4-piperidyl)-1,4,7,10-tetraazadecane, 1,4,7,10-tetrakis[2-(1,2,2,6,6-pentamethyl-4-piperidyloxy)-4-[N-(1,2,2,6,6-pentamethyl-4-piperidyl)-1,2,2,6,6-pentamethyl-4-piperidylamino]-triazin-6-yl]-1,10-bis(1,2,2,6,6-pentamethyl-4-piperidyl)-1,4,7,10-tetraazadecane, 1,4,7,10-tetrakis[2-(1,2,2,6,6-pentamethyl-4-piperidyloxy)-4-[N-(1,2,2,6,6-pentamethyl-4-piperidyl)-1,2,2,6,6-pentamethyl-4-piperidylamino]-triazin-6-yl]-1,10-bis(2,2,6,6-tetramethyl-4-piperidyl)-1,4,7,10-tetraazadecane, 1,4,7,10-tetrakis[2-(1,2,2,6,6-pentamethyl-4-piperidyloxy)-4-[N-(2,2,6,6-tetramethyl-4-piperidyl)-2,2,6,6-tetramethyl-4-piperidylamino]-triazin-6-yl]-1,10-bis(2,2,6,6-tetramethyl-4-piperidyl)-1,4,7,10-tetraazadodecane, 1,4,7,10-tetrakis[2-(2,2,6,6-tetramethyl-4-piperidyloxy)-4-[N-(2,2,6,6-tetramethyl-4-piperidyl)-butylamino]-triazin-6-yl]-1,10-bis(2,2,6,6-tetramethyl-4-piperidyl)-1,4,7,10-tetraazadecane, 1,4,7,10-tetrakis[2-(1,2,2,6,6-pentamethyl-4-piperidyloxy)-4-[N-(1,2,2,6,6-pentamethyl-4-piperidyl)-butylamino]-triazin-6-yl]-1,10-bis(1,2,2,6,6-pentamethyl-4-piperidyl]-1,4,7,10-tetraazadecane, 1,4,7,10-tetrakis[2-(1,2,2,6,6-pentamethyl-4-piperidyloxy)-4-[N-(1,2,2,6,6-pentamethyl-4-piperidyl)-butylamino]-triazin-6-yl]-1,10-bis(2,2,6,6-tetramethyl-4-piperidyl]-1,4,7,10-tetraazadecane, 1,4,7,10-tetrakis[2-(1,2,2,6,6-pentamethyl-4-piperidyloxy)-4-[N-(2,2,6,6-tetramethyl-4-piperidyl)-butylamino]-triazin-6-yl]-1,10-bis(2,2,6,6-tetramethyl-4-piperidyl]-1,4,7,10-tetraazadecane, 1,4,7,10-tetrakis[2-(2,2,6,6-tetramethyl-4-piperidyloxy)-4-[N-(2,2,6,6-tetramethyl-4-piperidyl)-butylamino]-triazin-6-yl]-1,4,7,10-tetraazadecane, 1,4,7,10-tetrakis[2-(1,2,2,6,6-pentamethyl-4-piperidyloxy)-4-[N-(1,2,2,6,6-pentamethyl-4-piperidyl)-butylamino]-triazin-6-yl]-1,4,7,10-tetraazadecane, 1,8,15-tris[2,4-bis(2,2,6,6-tetramethyl-4-piperidyloxy)triazin-6-yl]-1,15-bis(2,2,6,6-tetramethyl-4-piperidyl)-1,8,15-triazapentadecane, 1,8,15-tris[2,4-bis(1,2,2,6,6-pentamethyl-4-piperidyloxy)triazin-6-yl]-1,15-bis(1,2,2,6,6-pentamethyl-4-piperidyl)-1,8,15-triazapentadecane, 1,8,15-tris[2,4-bis(1,2,2,6,6-pentamethyl-4-piperidyloxy)triazin-6-yl]-1,15-bis(2,2,6,6-tetramethyl-4-piperidyl)-1,8,15-triazapentadecane, 1,8,15-tris[2,4-bis(2,2,6,6-tetramethyl-4-piperidyloxy)triazin-6-yl]-1,8,15-triazapentadecane, 1,8,15-tris[2,4-bis(1,2,2,6,6-pentamethyl-4-piperidyloxy)triazin-6-yl]-1,8,15-triazapentadecane, 1,8,15-tris[2-(2,2,6,6-tetramethyl-4-piperidyloxy)-4-[N-(2,2,6,6-tetramethyl-4-piperidyl)-2,2,6,6-tetramethyl-4-piperidylamino]-triazin-6-yl]-1,15-bis(2,2,6,6-tetramethyl-4-piperidyl)-1,8,15-triazapentadecane, 1,8,15-tris[2-(1,2,2,6,6-pentamethyl-4-piperidyloxy)-4-[N-(1,2,2,6,6-pentamethyl-4-piperidyl)-1,2,2,6,6-pentamethyl-4-piperidylamino]-triazin-6-yl]-1,15-bis(1,2,2,6,6-pentamethyl-4-piperidyl)-1,8,15-triazapentadecane, 1,8,15-tris[2-(1,2,2,6,6-pentamethyl-4-piperidyloxy)-4-[N-(1,2,2,6,6-pentamethyl-4-piperidyl)-1,2,2,6,6-pentamethyl-4-piperidylamino]-triazin-6-yl]-1,15-bis(2,2,6,6-tetramethyl-4-piperidyl)-1,8,15-triazapentadecane, 1,8,15-tris[2-(2,2,6,6-tetramethyl-4-piperidyloxy)-4-[N-(2,2,6,6-tetramethyl-4-piperidyl)-2,2,6,6-tetramethyl-4-piperidylamino]-triazin-6-yl]-1,8,15-triazapentadecane, 1,8,15-tris[2-(1,2,2,6,6-pentamethyl-4-piperidyloxy)-4-[N-(1,2,2,6,6-pentamethyl-4-piperidyl)-1,2,2,6,6-pentamethyl-4-piperidylamino]-triazin-6-yl]-1,8,15-triazapentadecane, 1,4,7-tris[2,4-bis(1,2,2,6,6-pentamethyl-4-piperidyloxy)triazin-6-yl]-1,7-bis(2,2,6,6-tetramethyl-4-piperidyl)-1,4,7-triazaheptane, 1,4,7-tris[2,4-bis(1,2,2,6,6-pentamethyl-4-piperidyloxy)triazin-6-yl]-1,4,7-triazaheptane, 1,5,9-tris[2,4-bis(2,2,6,6-tetramethyl-4-piperidyloxy)triazin-6-yl]-1,9-bis(2,2,6,6-tetramethyl-4-piperidyl)-1,5,9-triazanonane, 1,5,9-tris[2,4-bis(1,2,2,6,6-pentamethyl-4-piperidyloxy)triazin-6-yl]-1,9-bis(1,2,2,6,6-pentamethyl-4-piperidyl)-1,5,9-triazanonane, 1,5,9-tris[2,4-bis(1,2,2,6,6-pentamethyl-4-piperidyloxy)triazin-6-yl]-1,9-bis(2,2,6,6-tetramethyl-4-piperidyl)-1,5,9-triazanonane, 1,5,9-tris[2,4-bis(2,2,6,6-tetramethyl-4-piperidyloxy)-triazin-6-yl]-1,5,9-triazanonane, 1,5,9-tris[2,4-bis(1,2,2,6,6-pentamethyl-4-piperidyloxy)-triazin-6-yl]-1,5,9-triazanonane, 1,4,7-tris[2-(2,2,6,6-tetramethyl-4-piperidyloxy)-4-[N-(2,2,6,6-tetramethyl-4-piperidyl)-2,2,6,6-tetramethyl-4-piperidylamino]-triazin-6-yl]-1,7-bis(2,2,6,6-tetramethyl-4-piperidyl)-1,4,7-triazaheptane, 1,4,7-tris[2-(1,2,2,6,6-pentamethyl-4-piperidyloxy)-4-[N-(1,2,2,6,6-pentamethyl-4-piperidyl)-1,2,2,6,6-pentamethyl-4-piperidylamino]-triazin-6-yl]-1,7-bis(1,2,2,6,6-pentamethyl-4-piperidyl)-1,4,7-triazaheptane, 1,4,7-tris[2-(1,2,2,6,6-pentamethyl-4-piperidyloxy)-4-[N-(1,2,2,6,6-pentamethyl-4-piperidyl)-1,2,2,6,6-pentamethyl-4-piperidylamino]-triazin-6-yl]-1,7-bis(2,2,6,6-tetramethyl-4-piperidyl)-1,4,7-triazaheptane, 1,4,7-tris[2-(1,2,2,6,6-pentamethyl-4-piperidyloxy)-4-[N-(2,2,6,6-tetramethyl-4-piperidyl)2,2,6,6-tetramethyl-4-piperidylamino]-triazin-6-yl]-1,7-bis(2,2,6,6-tetramethyl-4-piperidyl)-1,4,7-triazaheptane, 1,4,7-tris[2-(2,2,6,6-tetramethyl-4-piperidyloxy)-4-[N-(2,2,6,6-tetramethyl-4-piperidyl)-2,2,6,6-tetramethyl-4-piperidylamino]-triazin-6-yl]-1,4,7-triazaheptane, 1,4,7-tris[2-(1,2,2,6,6-pentamethyl-4-piperidyloxy)-4-[N-(1,2,2,6,6-pentamethyl-4-piperidyl)-1,2,2,6,6-pentamethyl-4-piperidylamino]-triazin-6-yl]-1,4,7-triazaheptane, 1,5,9-tris[2-(2,2,6,6-tetramethyl-4-piperidyloxy)-4-[N-(2,2,6,6-tetramethyl-4-piperidyl)-2,2,6,6-tetramethyl-4-piperidylamino]-triazin-6-yl]-1,9-bis(2,2,6,6-tetramethyl-4-piperidyl)-1,5,9-triazanonane, 1,5,9-tris[2-(1,2,2,6,6-pentamethyl-4-piperidyloxy)-4-[N-(1,2,2,6,6-pentamethyl-4-piperidyl)-1,2,2,6,6,-pentamethyl-4-piperidylamino]-triazin-6-yl]-1,9-bis(1,2,2,6,6-pentamethyl-4-piperidyl)-1,5,9-triazanonane, 1,5,9-tris[2-(1,2,2,6,6-pentamethyl-4-piperidyloxy)-4-[N-(1,2,2,6,6-pentamethyl-4-piperidyl)-1,2,2,6,6-pentamethyl-4-piperidylamino]-triazin-6-yl]-1,9-bis(2,2,6,6-tetramethyl-4-piperidyl)-1,5,9-triazanonane, 1,5,9-tris[2-(1,2,2,6,6-pentamethyl-4-piperidyloxy)-4-[N-(2,2,6,6-tetramethyl-4-piperidyl)-2,2,6,6-tetramethyl-4-piperidylamino]-triazin-6-yl]-1,9-bis(2,2,6,6-tetramethyl-4-piperidyl)-1,5,9-triazanonane, 1,5,9-tris[2-(2,2,6,6-tetramethyl-4-piperidyloxy)-4-[N-(2,2,6,6-tetramethyl-4-piperidyl)-2,2,6,6-tetramethyl-4-piperidylamino]-triazin-6-yl]-1,5,9-triazanonane, 1,5,9-tris[2-(1,2,2,6,6-pentamethyl-4-piperidyloxy)-4-[N-(1,2,2,6,6-pentamethyl-4-piperidyl)-1,2,2,6,6-pentamethyl-4-piperidylamino]-triazin-6-yl]-1,5,9-triazanonane, 1,4,7-tris[2-(2,2,6,6-tetramethyl-4-piperidyloxy)-4-[N-(2,2,6,6-tetramethyl-4-piperidyl)-butylamino]-triazin-6-yl]-1,7-bis(2,2,6,6-tetramethyl-4-piperidyl)-1,4,7-triazaheptane, 1,4,7-tris[2-(1,2,2,6,6-pentamethyl-4-piperidyloxy)-4-[N-(1,2,2,6,6-pentamethyl-4-piperidyl)-butylamino]-triazin-6-yl]-1,7-bis(1,2,2,6,6-pentamethyl-4-piperidyl)-1,4,7-triazaheptane, 1,5,9-tris[2-(2,2,6,6-tetramethyl-4-piperidyloxy)-4-[N-(2,2,6,6-tetramethyl-4-piperidyl)-butylamino]-triazin-6-yl]-1,9-bis(2,2,6,6-tetramethyl-4-piperidyl)-1,5,9-triazanonane, 1,5,9-tris[2-(1,2,2,6,6-pentamethyl-4-piperidyloxy)-4-[N-(1,2,2,6,6-pentamethyl-4-piperidyl)-butylamino]-triazin-6-yl]-1,9-bis(1,2,2,6,6-pentamethyl-4-piperidyl)-1,5,9-triazanonane, 1,8-bis[2,4-bis(1,2,2,6,6-pentamethyl-4-piperidyloxy)triazin-6-yl]-1,8-diazaoctane, 1,5-bis[2,4-bis(1,2,2,6,6-pentamethyl-4-piperidyloxy)triazin-6-yl]-1,5-diazapentane, 1,4-bis[2,4-bis(1,2,2,6,6-pentamethyl-4-piperidyloxy)triazin-6-yl]-1,4-diazabutane, 1,5-bis[2,4-bis(1,2,2,6,6-pentamethyl-4-piperidyloxy)triazin-6-yl]-1,5-bis(1,2,2,6,6-pentamethyl-4-piperidyl)-1,5-diazapentane, 1,4-bis[2,4-bis(1,2,2,6,6-pentamethyl-4-piperidyloxy)triazin-6-yl]-1,4-bis(1,2,2,6,6-pentamethyl-4-piperidyl)-1,4-diazabutane, 1,5-bis[2,4-bis(1,2,2,6,6-pentamethyl-4-piperidyloxy)triazin-6-yl]-1,5-bis(2,2,6,6-tetramethyl-4-piperidyl)-1,5-diazapentane, 1,4-bis[2,4-bis(1,2,2,6,6-pentamethyl-4-piperidyloxy)triazin-6-yl]-1,4-bis(2,2,6,6-tetramethyl-4-piperidyl)-1,4-diazabutane, 1,8-bis[2-(2,2,6,6-tetramethyl-4-piperidyloxy)-4-[N-(2,2,6,6-tetramethyl-4-piperidyl)-2,2,6,6-tetramethyl-4-piperidylamino]-triazin-6-yl]-1,8-bis(2,2,6,6-tetramethyl-4-piperidyl)-1,8-diazaoctane, 1,8-bis[2-(1,2,2,6,6-pentamethyl-4-piperidyloxy)-4-[N-(1,2,2,6,6-pentamethyl-4-piperidyl)-1,2,2,6,6-pentamethyl-4-piperidylamino]-triazin-6-yl]-1,8-bis(2,2,6,6-tetramethyl-4-piperidyl)-1,8-diazaoctane and 1,8-bis[2-(1,2,2,6,6-pentamethyl-4-piperidyloxy)-4-[N-(1,2,2,6,6-pentamethyl-4-piperidyl)-1,2,2,6,6-pentamethyl-4-piperidylamino]-triazin-6-yl]-1,8-bis(1,2,2,6,6-pentamethyl- 4-piperidyl)-1,8-diazaoctane.

As mentioned at the outset, the compounds of the formula (I) are highly effective in improving the light stability, heat stability and oxidation stability of organic materials, in particular synthetic polymers and copolymers.

Examples of such organic materials which can be stabilized are:

1. Polymers of monoolefins and diolefins, for example polypropylene, polyisobutylene, polybut-1-ene, poly4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPF/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly($\alpha$-methylstyrene).

6. Copolymers of styrene or $\alpha$-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer, and block copolymers of styrene such as styrene/butadiene/styrene, styrene/isoprene/styrene, styrene/ethylene/butylene/styrene or styrene/ethylene/propylene/styrene.

7. Graft copolymers of styrene or $\alpha$-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from $\alpha,\beta$-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4, -trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, polyisocyanates or epoxy resins.

26. Crosslinked epoxy resins derived from polyepoxides, for example from bisglycidyl ethers or from cycloaliphatic diepoxides.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

The compounds of the formula (I) can be used in mixtures with organic materials in various proportions depending on the nature of the material to be stabilized, on the end use and on the presence of other additives.

In general, it is appropriate to use, for example, 0.01 to 5% by weight, of the compounds of the present invention, relative to the weight of the material to be stabilized, preferably between 0.05 and 1%.

In general the compounds of the present invention can be added to the polymeric materials before, during or after the polymerisation or crosslinking of the said materials.

The compounds of the present invention can be incorporated in the polymeric materials in the pure form or encapsulated in waxes, oils or polymers.

The compounds of the present invention can be incorporated in the polymeric materials by various processes, such as dry mixing in the form of powder, or wet mixing in the form of solutions or suspensions or also in the form of a masterbatch; in such operations, the polymer can be used in the form of powder, granules, solutions, suspensions or in the form of latices.

The materials stabilized with the products of the present invention can be used for the production of mouldings, films, tapes, monofilaments, fibres, surface coatings and the like.

If desired, other conventional additives for synthetic polymers, such as antioxidants, UV absorbers, nickel stabilizers, pigments, fillers, plasticizers, antistatic agents, flameproofing agents, lubricants, corrosion inhibitors and metal deactivators, can be added to the mixtures of the compounds of the present invention with the organic materials.

Particular examples of additives which can be used in admixture with the compounds of the formula (I) are:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-di-methyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-do-decylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis-(2,6-dimethyl-4-hydroxyphenyl) disulfide.

1.5. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy2-methylphenyl)pentane.

1.6. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tris-(3,5-di-tert-butyl-4-hydroxybenzyl)amine, bis(4-tert-butyl-3-hydroxy-2,6-dimethylbenzyl)dithioterephthalate, bis(3,5-ditert-butyl-4-hydroxybenzyl)sulfide, isooctyl-3,5di-tert-butyl-4-hydroxybenzylmercaptoacetate.

1.7. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl4-hydroxybenzyl)malonate, bis[4-(1,1,3,3-tetramethylbutyl)phenyl]-2,2-bis(3,5-di-tert-butyl-4-hydroxybenzyl)malonate.

1.8. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.9. Triazine Compounds, for example 2,4-bis (octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris (3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl) isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.10. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy3-methylbenzylphosphonate, the calcium salt of the monoethyl ester of 3,5-di-tert-butyl-4-hydroxybenzylphosphonic acid.

1.11. Acylaminophenols, for example 4-hydroxylauranilide, 4-hydroxystearanilide, octyl N-(3,5-di-tert-butyl-4-hydroxyphenyl)carbamate.

1.12. Esters of β-(3,5-di-tert-butyl-4-hydroxyphenyl) propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.13. Esters of β-(5-tert-butyl-4-hydroxy-3-methylphenyl)propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis-(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14 Esters of β-(3,5-dicyclohexyl-4-hydroxyphenyl) propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15 Esters of 3,5-di-tert-butyl-4-hydroxyphenyl acetic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis (hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Amides of β-(3,5-di-tert-butyl-4-hydroxyphenyl) propionic acid e.g. N,N'-bis(3,5-di-tert-butyl-4-hydroxyphenylpropionyl)hexamethylenediamine, N,N'-bis (3,5-di-tert-butyl-4-hydroxyphenylpropionyl) trimethylenediamine, N,N'-bis(3,5-tert-butyl-4-hydroxyphenylpropionyl)hydrazine.

2. UV absorbers and light stabilisers 2.1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl) benzotriazole, 2-(2'-hydroxy-4'-octyloxyphenyl) benzotriazole, 2-(3',5'-di-tert-amyl-2'-hydroxyphenyl) benzotriazole, 2-(3',5'-bis-(α,α-dimethylbenzyl)-2'-hydroxyphenyl)benzotriazole, mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl) phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl) benzotriazole, 2-(3'-tert-butyl-5'-[2-(2-ethylhexyloxy) carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl) phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—$CH_2CH_2$—COO$(CH_2)_3$—]$_2$, where R=3'-tert-butyl-4'-hydroxy-5'-2H-benzotriazol-2-ylphenyl.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tert butylphenyl salicylate, phenyl salicylate, octylphenyl salicylate, dibenzoyl resorcinol, bis (4-tert-butylbenzoyl) resorcinol, benzoyl resorcinol, 2,4-di-tertbutylphenyl 3,5-di-tert-butyl-4-hydroxybenzoate, hexadecyl 3,5-di-tert-butyl-4-hydroxybenzoate, octadecyl 3,5-di-tert butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-piperidyl)sebacate, bis(2,2,6,6-tetramethyl-piperidyl)succinate, bis(1,2,2,6,6-pentamethylpiperidyl) sebacate, bis(1,2,2,6,6-pentamethylpiperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl) hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butane-tetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decan-2,4-dion, bis(1-octyloxy-2,2,6,6-tetramethylpiperidyl) sebacate, bis(1-octyloxy-2,2,6,6-tetramethylpiperidyl) succinate, the condensate of N,N'-bis-(2,2,6,6-tetramethyl-4-piperidyl)hexamethylenediamine and 4-morpholino-2,6-dichloro-1,3,5-triazine, the condensate of 2-chloro-4,6-bis (4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl) pyrrolidine-2,5-dione.

2.7. Oxamides, for example 4,4'-dioctyloxyoxanilide, 2,2'-dioctyloxy-5,5'-di-tert-butoxanilide, 2,2'-didodecyloxy-5,5'-di-tert-butoxanilide, 2-ethoxy-2'-ethoxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide and mixtures of ortho- and paramethoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis (2,4-dimethylphenyl)-1,3,5-triazine, 2-[2-hydroxy-4-(2hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl) oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite; trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl) methylphosphite, bis(2,4-di-tert-butyl-6-methylphenyl) ethylphosphite.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N,N-dialkylhydroxylamine derived from hydrogenated tallow amine.

7. Polyamide stabilisers, for example, copper salts in combination with iodides and/or phosphorus compounds and salts of divalent manganese.

8. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or tin pyrocatecholate.

9. Nucleating agents, for example, 4-tert-butylbenzoic acid, adipic acid, diphenylacetic acid.

10. Fillers and reinforcing agents, for example, calcium carbonate, silicates, glass fibres, asbestos, talc, kaolin, mica, barium sulfate, metal oxides and hydroxides, carbon black, graphite.

11. Other additives, for example, plasticisers, lubricants, emulsifiers, pigments, optical brighteners, flameproofing agents, antistatic agents and blowing agents.

12. Benzofuranones and indolinones, for example those disclosed U.S. Pat. No. 4,325,863, U.S. Pat. No. 4,338,244 or U.S. Pat. No. 5,175,312, or 3-[4-(2-acetoxyethoxy) phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl) benzofuran-2-one], 5,7-di-tert-butyl-3-(4-ethoxyphenyl) benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5, 7-di-tert-butyl-benzofuran-2-one.

The compounds of the formula (I) can also be used as stabilizers, especially as light stabilizers, for almost all materials known in the art of photographic reproduction and other reproduction techniques as e.g. described in Research Disclosure 1990, 31429 (pages 474 to 480).

In the examples which follow the preparation of some compounds of the formula (I) according to the process of the present invention is described; these examples are given for illustrative purposes and do not imply any limitation.

EXAMPLE 1

Preparation of the compound of the formula

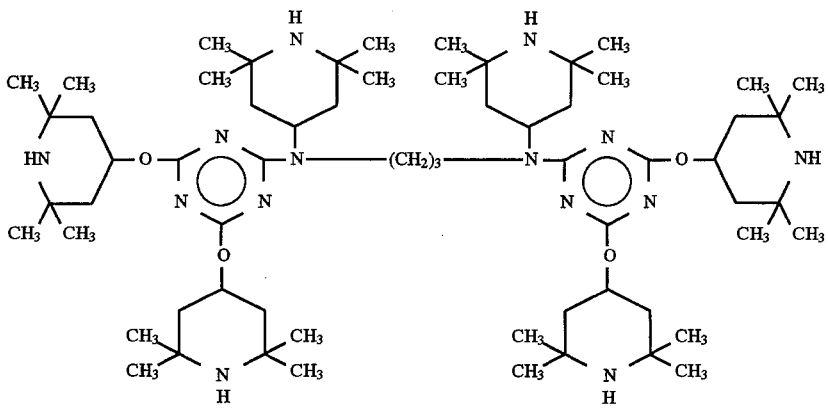

36.9 g (0.2 mol) of cyanuric chloride are added over 90 minutes to a mixture, maintained at 0° C., of 25.6 g (0.8 mol) of methanol and 94.3 g (0.6 mol) of 2,2,6,6-tetramethyl-4-piperidinol in 100 ml of xylene.

After the end of the addition, stirring is continued for 5 hours at 10° C.

To the mixture thus obtained, 34.2 g (0.097 mol) of 1,5-bis(2,2,6,6-tetramethyl-4-piperidyl)-1,5-diazapentane are added, and the mixture is heated for 2 hours at 100° C., the unreacted methanol being distilled off.

The mixture is cooled to 60° C., 111.6 g of a 30% solution of sodium methoxide (0.62 mol) in methanol are added and the mixture is heated up to 135° C., the added methanol being distilled off, and this is followed by hearing at 135° C. for 8 hours, the methanol formed being separated off.

After cooling to 60° C., the reaction mixture is diluted with 200 ml of xylene, washed with water until complete removal of chlorine ions and dried by hearing at 200° C. under reduced pressure, in order to separate off the unreacted 2,2,6,6-tetramethyl-4-piperidinol.

50 ml of toluene to a mixture, maintained at −10° C., of 51.6 g (0.28 mol) of cyanuric chloride and 99.1 g (0.63 mol) of 2,2,6,6-tetramethyl-4-piperidinol in 500 ml of toluene.

After the end of the addition, stirring is continued for 30 minutes at −10° C. and for 3 hours at 20° C.

151.2 g of a 30% solution of sodium methoxide (0.84 mol) in methanol are then added, the temperature rising up to 60° C.

Stirring is continued for 90 minutes, allowing the temperature to drop down to 30° C.

0.8 g of lithium amide is added, the mixture is heated up to 130° C. while removing the methanol and the major part of the toluene, and hearing is continued at 130° C. for 18 hours, the methanol formed being separated off.

After cooling to 60° C., 300 ml of toluene are added and the solution obtained is washed with water until complete removal of chlorine ions and dried in vacuo.

This gives 150.8 g (yield 95.2% of theory) of a product melting at 178°–179° C. and having a purity of 98.9% as determined by HPLC.

EXAMPLE 3

The compound of the formula

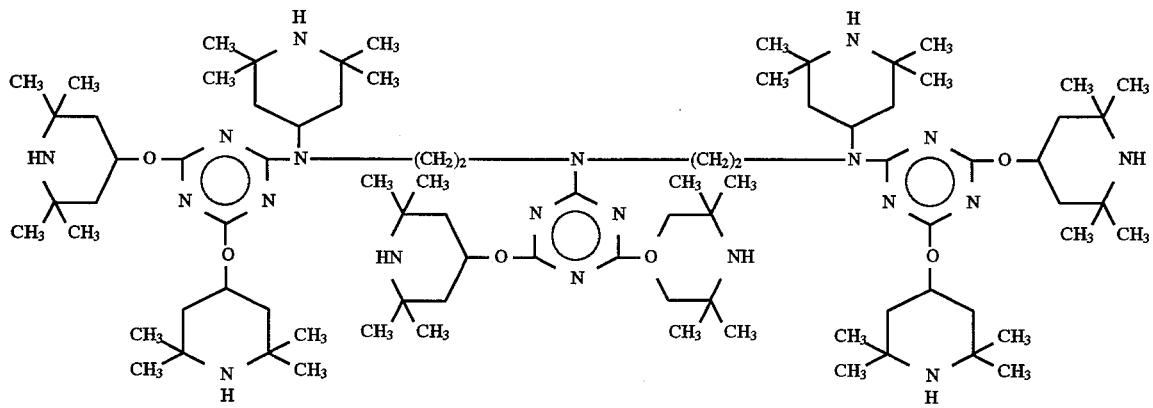

This gives 101.5 g (yield 92.5% of theory) of a product melting at 178°–179° C. and having a purity of 99.4% as determined by HPLC.

EXAMPLE 2

The same compound as in Example 1 is prepared by adding, over 45 minutes, a solution of 49.4 g (0.14 mol) of 1,5-bis(2,2,6,6-tetramethyl-4-piperidyl)-1,5-diazapentane in is prepared as described in Example 1, using an appropriate molar quantity of 1,7-bis(2,2,6,6-tetramethyl-4-piperidyl)-1,4,7-triazapentane, replacing the 1,5-bis(2,2,6,6-tetramethyl-4-piperidyl)-1,5-diazapentane.

After crystallisation from octane (yield 90.4% of theory), the product obtained melts at 133°–134° C. and has a purity of 99% as determined by HPLC.

EXAMPLE 4

Preparation of the compound of the formula

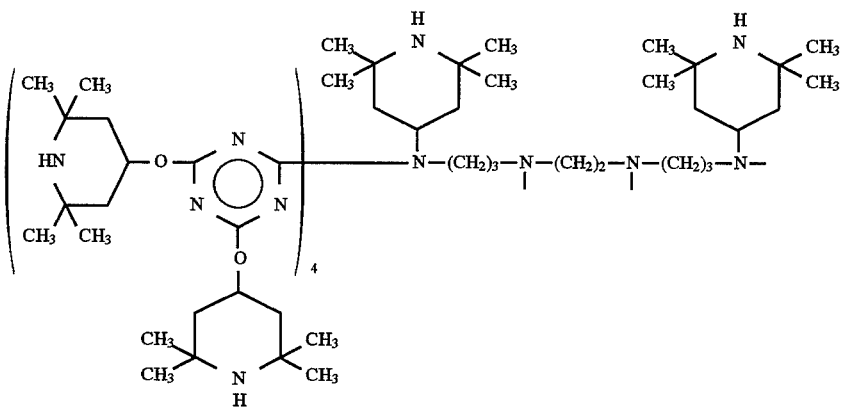

A solution of 31.7 g (0.07 mol) of 1,12-bis(2,2,6,6-tetramethyl-4-piperidyl)-1,5,8,12-tetraazadodecane in 30 ml of xylene is added over 45 minutes to a mixture, maintained at −10° C., of 51.6 g (0.28 mol) of cyanuric chloride and 127.4 g (0.81 mol) of 2,2,6,6-tetramethyl-4-piperidinol in 500 ml of a 1:1 mixture by volume of xylene and t-amyl alcohol.

After the end of the addition, stirring is continued for 45 minutes at −10° C. and for 3 hours at 20° C.

151.2 g of a 30% solution of sodium methoxide (0.84 mol) in methanol are then added over 1 hour, the temperature rising up to 60° C.

Stirring is continued for 90 minutes, allowing the temperature to drop down to 30° C.

0.8 g of lithium amide is added, the mixture is heated up to 135° C., the more volatile solvents being distilled off, and hearing is continued at 135° C. for 10 hours, the methanol formed being removed.

The reaction mixture is cooled to 60° C., diluted with 200 ml of xylene, washed with water until complete removal of chlorine ions and dried by hearing up to 200° C. under reduced pressure in order to separate off the unreacted 2,2,6,6-tetramethyl-4-piperidinol.

The residue obtained is crystallised from octane. This gives 131.8 g (yield 93.6% of theory) of a product melting at 140°–141° C. and having a purity of 99.2% as determined by HPLC.

EXAMPLE 5

The same compound as in Example 4 is prepared by hearing a mixture of 22.6 g (0.05 mol) of 1,12-bis(2,2,6,6-tetramethyl-4-piperidyl)-1,5,8,12-tetraazadodecane, 35.1 g (0.2 mol) of 2-chloro-4,6-dimethoxy-1,3,5-triazine and 94.3 g (0.6 mol) of 2,2,6,6-tetramethyl-4-piperidinol in 400 ml of xylene for 2 hours at 100° C.

After cooling to 40° C., a solution of 8 g (0.2 mol) of sodium hydroxide in 50 ml of water is added, the mixture is heated up to 80° C. and the aqueous phase is separated off.

After azeotropic removal of the residual water, 0.9 g of sodium methoxide is added and the mixture is heated at 135° C. for 8 hours, the methanol formed being removed.

The reaction mixture is cooled to 60° C., washed with water until complete removal of chlorine ions and dried by hearing up to 200° C. under reduced pressure, in order to separate off the unreacted 2,2,6,6-tetramethyl-4-piperidinol.

The residue obtained is crystallised from octane. This gives 92.9 g (yield 92.4% of theory) of a product melting at 140°–141° C. and having a purity of 99% as determined by HPLC.

EXAMPLE 6

The same compound as in Example 4 is prepared as described in Example 1, using an appropriate molar quantity of 1,12-bis(2,2,6,6-tetramethyl-4-piperidyl)-1,5,8,12-tetraazadodecane, replacing the 1,5-bis(2,2,6,6-tetramethyl-4-piperidyl)-1,5-diazapentane.

After crystallisation from octane, the product obtained (yield 89.2% of theory) melts at 139°–141° C. and has a purity of 98.9% as determined by HPLC.

EXAMPLES 7–11

Following the procedure described in Example 4 and using the appropriate reagents in the appropriate molar ratios, the following compounds of the formula (I) are prepared:

| Example | $R_1$ | m | $R_2$ | $R_3$ | m.p.(° C.) |
|---|---|---|---|---|---|
| 7 | H | 2 | (2,2,6,6-tetramethyl-4-piperidyl)-O— | —C—(CH$_2$)$_6$—N— with two tetramethylpiperidyl groups | 236–237 |

-continued

| Example | $R_1$ | m | $R_2$ | $R_3$ | m.p.(° C.) |
|---|---|---|---|---|---|
| 8 | $CH_3$ | 2 | (2,2,6,6-tetramethyl-1-methyl-piperidin-4-yl)oxy | $-C-(CH_2)_6-N-$ bis(2,2,6,6-tetramethylpiperidin-4-yl) | 242–243 |
| 9 | H | 3 | (2,2,6,6-tetramethylpiperidin-4-yl)oxy | $-C-(CH_2)_6-N-(CH_2)_6-N-$ bis(2,2,6,6-tetramethylpiperidin-4-yl) | 73–74 |
| 10 | $CH_3$ | 4 | (2,2,6,6-tetramethyl-1-methyl-piperidin-4-yl)oxy | $-C-(CH_2)_3-N-(CH_2)_2-N-(CH_2)_3-N-$ bis(2,2,6,6-tetramethylpiperidin-4-yl) | 143–145 |
| 11 | $CH_3$ | 2 | (2,2,6,6-tetramethyl-1-methyl-piperidin-4-yl)oxy | $-C-(CH_2)_6-N-$ bis(2,2,6,6-tetramethylpiperidin-4-yl) | 219–220 |

What is claimed is:

1. A process for the preparation of a compound of the formula (I)

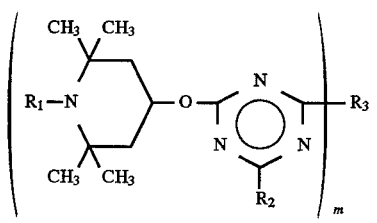

in which $R_1$ is hydrogen, $C_1$–$C_8$alkyl, $C_1$–$C_{18}$alkoxy, $C_5$–$C_{12}$cycloalkoxy, $C_3$–$C_6$alkenyl or $C_7$–$C_9$phenylalkyl which is unsubstituted or mono-, di- or tri-substituted on the phenyl by $C_1$–$C_4$alkyl; $R_2$ is a group of the formula (II)

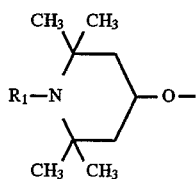

or a group

where $R_4$ and $R_5$ which can be identical or different are hydrogen, $C_1$–$C_{18}$alkyl, $C_5$–$C_{12}$cycloalkyl which is unsubstituted or mono-, di- or tri-substituted by $C_1$–$C_4$alkyl; $C_7$–$C_9$phenylalkyl which is unsubstituted or mono-, di- or tri-substituted on the phenyl by $C_1$–$C_4$alkyl; tetrahydrofurfuryl, $C_2$–$C_4$alkyl substituted in the 2-, 3- or 4-position by $C_1$–$C_8$alkoxy or by di($C_1$–$C_4$alkyl)amino; or a group of the formula (III)

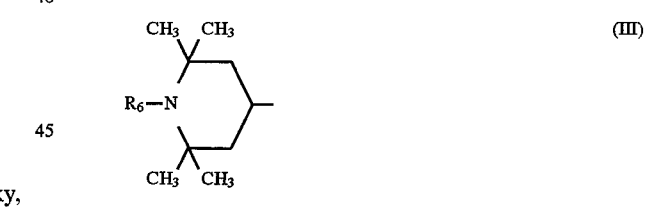

where $R_6$ is as defined for $R_1$, or

is a 5- to 7-membered heterocyclic group, m is an integer from 2 to 6 and, if m is 2, $R_3$ is one of the groups of the formulae (IVa)–(IVc)

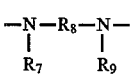

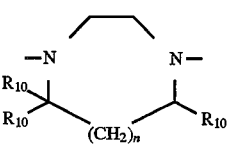

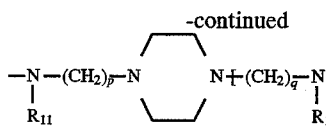 (IVc)

in which $R_7$, $R_9$, $R_{11}$ and $R_{12}$ which can be identical or different are hydrogen, $C_1$–$C_{18}$alkyl, $C_5$–$C_{12}$cycloalkyl which is unsubstituted or mono-, di- or tri-substituted by $C_1$–$C_4$alkyl; $C_7$–$C_9$phenylalkyl which is unsubstituted or mono-, di- or tri-substituted on the phenyl by $C_1$–$C_4$alkyl; or a group of the formula (III), $R_8$ is $C_2$–$C_{12}$alkylene, $C_4$–$C_{12}$alkylene interrupted by 1, 2 or 3 oxygen atoms; $C_5$–$C_7$cycloalkylene, $C_5$–$C_7$cycloalkylenedi($C_1$–$C_4$alkylene), $C_1$–$C_4$alkylenedi($C_5$–$C_7$cycloalkylene), phenylene or xylylene, $R_{10}$ is hydrogen or methyl, n is zero or 1, p and q which can be identical or different are integers from 2 to 6 and r is zero or 1, and, if m is 3, 4, 5 or 6, $R_3$ is a group of the formula (V)

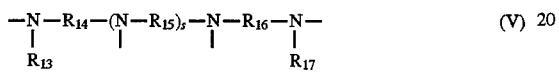 (V)

in which $R_{13}$ and $R_{17}$ which can be identical or different are as defined above for $R_7$, $R_9$, $R_{11}$ and $R_{12}$; $R_{14}$, $R_{15}$ and $R_{16}$ which can be identical or different are $C_2$–$C_6$alkylene and s is zero, 1, 2 or 3, and, if m is 3, $R_3$ can also be a group of the formula (VIa) or (VIb)

 (VIa)

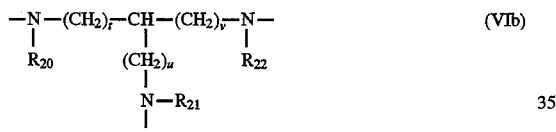 (VIb)

in which $R_{18}$ is $C_2$–$C_6$alkylene, $R_{19}$, $R_{20}$, $R_{21}$ and $R_{22}$ which can be identical or different are as defined above for $R_7$, $R_9$, $R_{11}$ and $R_{12}$, t and v which can be identical or different are integers from 2 to 6 and u is zero or 1, this process comprising:

I-a) the reaction of cyanuric chloride with a $C_1$–$C_4$alkanol and, if $R_2$ is a group

also a compound of the formula (VII)

 (VII)

in which $R_4$ and $R_5$ are as defined above, in the presence of a compound of the formula (VIII) as HCl interceptor

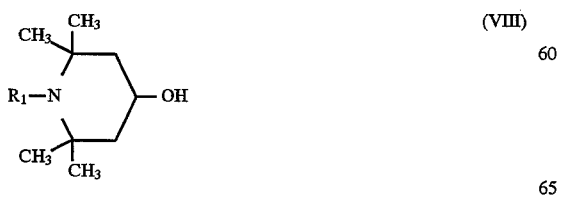 (VIII)

in which $R_1$ is as defined above, to give an intermediate of the formula (IX)

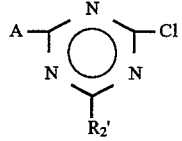 (IX)

in which A is $C_1$–$C_4$alkoxy and $R_2$ is $C_1$–$C_4$alkoxy or, if $R_2$ is a group

$R_2'$ is

;

I-b) the reaction of the intermediate of the formula (IX) with a compound of the formula (X)

 (X)

in which $R_3$ and m are as defined above, to give—after neutralisation of the reaction mixture with sodium hydroxide, potassium hydroxide, sodium $C_1$–$C_4$alkoxide or potassium $C_1$–$C_4$alkoxide—an intermediate of the formula (XI)

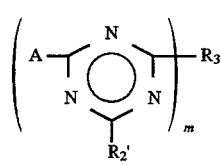 (XI)

together with a compound of the formula (VIII) as the free base; and

I-c) the reaction of the intermediate of the formula (XI) with a compound of the formula (VIII) in the presence of a transesterification catalyst; or comprising II-a) the reaction of cyanuric chloride with a compound of the formula (X) and, if $R_2$ is a group

also with a compound of the formula (VII), in the presence of a compound of the formula (VIII) as HCl interceptor to give an intermediate of the formula (XII)

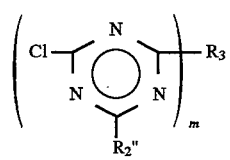 (XII)

in which $R_2''$ is Cl or, if $R_2$ is a group

R₂″ is

and m and R₃ are as defined above;

II-b) the reaction of the intermediate of the formula (XII) with sodium $C_1$–$C_4$alkoxide or potassium $C_1$–$C_4$alkoxide to give an intermediate of the formula (XI) together with a compound of the formula (VIII) as the free base; and II-c) the reaction of the intermediate of the formula (XI) with a compound of the formula (VIII) in the presence of a transesterification catalyst;

the reactions from I-a) to I-c) or from II-a) to II-c) being carried out at a temperature of between −20° C. and 180° C. in an inert organic solvent or, in the case of the reaction I-c) or II-c) also without solvent.

2. A process according to claim 1, wherein $R_1$ and $R_6$ which can be identical or different are hydrogen, $C_1$–$C_4$alkyl, $C_6$–$C_{12}$alkoxy, $C_5$–$C_8$cycloalkoxy, allyl or benzyl.

3. A process according to claim 1, wherein $R_2$ is a group of the formula (II) or a group

where $R_4$ and $R_5$ which can be identical or different are hydrogen, $C_1$–$C_{12}$alkyl, $C_5$–$C_8$cycloalkyl which is unsubstituted or mono-, di- or trisubstituted by $C_1$–$C_4$alkyl; benzyl, tetrahydrofurfuryl, $C_2$–$C_3$alkyl substituted in the 2- or 3-position by $C_1$–$C_4$alkoxy or by di($C_1$–$C_4$alkyl)amino; or a group of the formula (III), or

is 1-pyrrolidyl, 1-piperidyl, 4-morpholinyl, 4-methyl-1-piperazinyl or 1-hexahydroazepinyl, m is an integer from 2 to 6 and, if m is 2, $R_3$ is one of the groups of the formula (IVa)–(IVc) in which $R_7$, $R_9$, $R_{11}$ and $R_{12}$ which can be identical or different are hydrogen, $C_1$–$C_{12}$alkyl, $C_5$–$C_8$cycloalkyl which is unsubstituted or mono-, di- or tri-substituted by $C_1$–$C_4$alkyl; benzyl or a group of the formula (III), $R_8$ is $C_2$–$C_{10}$alkylene, $C_4$–$C_{10}$alkylene interrupted by 1, 2 or 3 oxygen atoms; cyclohexylene, cyclohexylenedimethylene, methylenedicyclohexylene or xylylene, $R_{10}$ is hydrogen or methyl, n is zero or 1, p and q which can be identical or different are an integer from 2 to 6 and r is zero or 1, and, if m is 3, 4, 5 or 6, $R_3$ is a group of the formula (V) in which $R_{13}$ and $R_{17}$ which can be identical or different are as defined above for $R_7$, $R_9$, $R_{11}$ and $R_{12}$; $R_{14}$, $R_{15}$ and $R_{16}$ which can be identical or different are $C_2$–$C_6$alkylene and s is zero or 1, 2 or 3, and, if m is 3, $R_3$ can also be a group of the formula (VIa) or (VIb) in which $R_{18}$ is $C_2$–$C_6$alkylene, $R_{19}$, $R_{20}$, $R_{21}$, $R_{22}$ which can be identical or different are as defined above for $R_7$, $R_9$, $R_{11}$ and $R_{12}$, t and v which can be identical or different are integers from 2 to 6 and u is zero or 1.

4. A process according to claim 1, wherein $R_2$ is a group of the formula (II) or a group

where $R_4$ and $R_5$ which can be identical or different are hydrogen, $C_1$–$C_{10}$alkyl, cyclohexyl which is unsubstituted or mono-, di- or tri-substituted by $C_1$–$C_4$alkyl; benzyl, tetrahydrofurfuryl, $C_2$–$C_3$alkyl substituted in the 2- or 3-position by methoxy, by ethoxy, by dimethylamino or by diethylamino; or a group of the formula (III), or

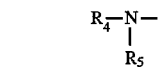

is 4-morpholinyl, m is an integer from 2 to 6 and, if m is 2, $R_3$ is one of the groups of the formulae (IVa)–(IVc) in which $R_7$, $R_9$, $R_{11}$ and $R_{12}$ which can be identical or different are hydrogen, $C_1$–$C_{10}$alkyl, cyclohexyl which is unsubstituted or mono-, di- or tri-substituted by $C_1$–$C_4$alkyl; benzyl or a group of the formula (III), $R_8$ is $C_2$–$C_8$alkylene, $C_4$–$C_{10}$alkylene interrupted by 1, 2 or 3 oxygen atoms; cyclohexylenedimethylene, methylenedicyclohexylene or xylylene, $R_{10}$ is hydrogen or methyl, n is zero or 1, p and q which can be identical or different are 2 or 3 and r is zero or 1 and, if m is 3, 4, 5 or 6, $R_3$ is a group of the formula (V) in which $R_{13}$ and $R_{17}$ which can be identical or different are as defined above for $R_7$, $R_9$, $R_{11}$ and $R_{12}$; $R_{14}$, $R_{15}$ and $R_{16}$ which can be identical or different are $C_2$–$C_6$alkylene and s is zero, 1, 2 or 3, and, if m is 3, $R_3$ can also be a group of the formula (VIa) or (VIb) in which $R_{18}$ is $C_2$–$C_3$alkylene, $R_{19}$, $R_{20}$, $R_{21}$ and $R_{22}$ which can be identical or different are as defined above for $R_7$, $R_9$, $R_{11}$ and $R_{12}$, t and v which can be identical or different are integers from 3 to 5 and u is zero or 1.

5. A process according to claim 1, wherein $R_2$ is a group of the formula (II) or a group

where $R_4$ and $R_5$ which can be identical or different are $C_1$–$C_8$alkyl, cyclohexyl, benzyl, tetrahydrofurfuryl, $C_2$–$C_3$alkyl substituted in the 2- or 3-position by methoxy, by ethoxy, by dimethylamino or by diethylamino; or a group of the formula (III), or $R_5$ can also be hydrogen, or

is 4-morpholinyl, m is 2, 3 or 4 and, if m is 2, $R_3$ is one of the groups of the formulae (IVa)–(IVc) in which $R_7$, $R_9$, $R_{11}$ and $R_{12}$ which can be identical or different are $C_1$–$C_4$alkyl, cyclohexyl or a group of the formula (III), $R_8$ is $C_2$–$C_6$alkylene, $C_6$–$C_{10}$alkylene interrupted by 2 or 3 oxygen atoms, cyclohexylenedimethylene, methylenedicyclohexylene or xylylene, $R_{10}$ is hydrogen, n is zero, p and q which can be identical or different are 2 or 3 and r is zero or 1, and, if m is 3 or 4, $R_3$ is a group of the formula (V) in which $R_{13}$ and $R_{17}$ which can be identical or different are as defined above for $R_7$, $R_9$, $R_{11}$ and $R_{12}$, $R_{14}$, $R_{15}$ and $R_{16}$ which can be identical or different are $C_2$–$C_6$alkylene and s is zero or 1.

6. A process according to claim 1, wherein $R_1$ is hydrogen or methyl $R_2$ is 2,2,6,6-tetramethyl-4-piperidyloxy or 1,2,2,6,6-pentamethyl-4-piperidyloxy, m is 2, 3 or 4 and, if m is 2. $R_3$ is a group of the formula (IVa) in which $R_7$ and $R_9$ which can be identical or different are cyclohexyl, 2,2,6,6-tetramethyl-4-piperidyl or 1,2,2,6,6-pentamethyl-4-piperidyl and $R_8$ is $C_2$–$C_6$alkylene, and, if m is 3 or 4, $R_3$ is a group of the formula (V) in which $R_{13}$ and $R_{17}$ which can be identical or different are as defined above for $R_7$ and $R_9$, $R_{14}$, $R_{15}$ and $R_{16}$ which can be identical or different are —$(CH_2)_{2-6}$ and s is zero or 1.

7. A process according to claim 1, wherein the $C_1$–$C_4$alkanol used is methanol, ethanol, propanol, n-butanol or isobutanol.

8. A process according to claim 1, wherein the sodium or potassium $C_1$–$C_4$alkoxide used is sodium methoxide or ethoxide.

9. A process according to claim 1, wherein the piperidinol of the formula (VIII) is used in an excess of from 10 to 50% over theory.

10. A process according to claim 1, wherein the transesterification catalyst used is an alkali metal or a $C_1$–$C_4$alkoxide, hydride or amide of an alkali metal.

11. A process according to claim 1, wherein the intermediates of the formulae (IX), (XI) and (XII) are not isolated from the reaction mixture.

12. A process according to claim 1, wherein one or more intermediates of the formulae (IX), (XI) and (XII) are used after they have been isolated from the reaction mixture.

13. A process according to claim 1, wherein the reaction solvent used is benzene, toluene, xylene, trimethylbenzene, tetrahydrofuran, dioxane, dibutyl ether, 1,2-dimethoxyethane, 1,2-diethoxyethane, bis(2-methoxyethyl) ether, bis(2-ethoxyethyl) ether or a mixture in any ratio of the aromatic hydrocarbons cited above with t-butyl alcohol or t-amyl alcohol.

14. A process according to claim 1, wherein the first stage of the reaction—reactions I-a) and II-a)—is carried out at a temperature of between −20° C. and 40° C., the second stage—reactions I-b) and II-b)—is carried out at a temperature of between 20° C. and 120° C., and the third stage—reactions I-c) and II-c)—is carried out at a temperature of between 120° C. and 180° C.).

15. A process according to claim 13 wherein ratio of aromatic hydrocarbons with t-butyl alcohol or t-amyl alcohol is 3:1 to 1:3 by volume.

* * * * *